(12) United States Patent
Park et al.

(10) Patent No.: US 8,318,402 B2
(45) Date of Patent: Nov. 27, 2012

(54) PHOTOSENSITIVE COMPOUND AND PHOTOSENSITIVE COMPOSITION INCLUDING THE SAME

(75) Inventors: Joo Hyeon Park, Seoul (KR); Seok Chan Kang, Seoul (KR); Jung Hwan Cho, Seoul (KR); Kyung Chul Son, Seoul (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 98 days.

(21) Appl. No.: 12/649,863

(22) Filed: Dec. 30, 2009

(65) Prior Publication Data

US 2011/0053084 A1  Mar. 3, 2011

(30) Foreign Application Priority Data

Aug. 31, 2009  (KR) .................. 10-2009-0081180

(51) Int. Cl.
*G03F 7/023* (2006.01)
*C07C 245/12* (2006.01)

(52) U.S. Cl. ......... 430/192; 430/193; 534/556; 534/557

(58) Field of Classification Search .................. 430/191, 430/192, 193; 534/556, 557
See application file for complete search history.

(56) References Cited

U.S. PATENT DOCUMENTS

| | | | | |
|---|---|---|---|---|
| 4,217,407 A | * | 8/1980 | Watanabe et al. | 430/166 |
| 5,238,775 A | * | 8/1993 | Kajita et al. | 430/192 |
| 5,413,896 A | * | 5/1995 | Kajita et al. | 430/192 |

* cited by examiner

*Primary Examiner* — John Chu
(74) *Attorney, Agent, or Firm* — Ladas & Parry LLP

(57) ABSTRACT

Disclosed are a photosensitive compound and a method of manufacturing the same. The photosensitive is composed of a naphthoquinonediazide sulfonic ester compound having at least one naphthoquinonediazide sulfoxy group, and having either at least one carboxy group with 1 to 8 carbon atoms or at least one alkoxy group with 1 to 8 carbon atoms, in one molecule.

4 Claims, No Drawings

PHOTOSENSITIVE COMPOUND AND PHOTOSENSITIVE COMPOSITION INCLUDING THE SAME

CROSS-REFERENCE TO RELATED APPLICATIONS

This application claims the benefit of Korean Patent Application No. 10-2009-0081180, filed on Aug. 31, 2009, in the Korean Intellectual Property Office, the disclosure of which is incorporated herein by reference.

BACKGROUND

1. Field of the Invention

The present invention relates to a photosensitive compound and a photosensitive composition including the same, and more particularly, to a photosensitive compound that may improve a solubility performance of an exposed portion while preventing a loss of an unexposed portion, thereby improving a pattern perpendicularity in a semiconductor photolithography process, and to a photosensitive composition including the photosensitive compound.

2. Description of the Related Art

In general, sulfonic ester may be used as a photosensitive material from among compositions used in a lithography process utilizing visible rays, ultraviolet rays, electron beams, ion beams, and x-rays.

A photosensitive composition may be prepared by dissolving the sulfonic ester and a resin capable of being dissolved in a basic aqueous solution in a solvent. The photosensitive composition may be heated to about 50° C. to 150° C. after being coated on a film, so that a residual solvent is easily eliminated. The film generated after the heating may be exposed using an exposurer, and developed using a developer to thereby obtain a desired pattern. In this instance, the sulfonic ester exposed in the ultraviolet rays may be transformed into a carboxylic acid more readily dissolved in a basic developer. In this manner, the desired pattern may be obtained using a development speed difference between an exposed portion and an unexposed portion.

The sulfonic ester may be diversely provided along with a complexity in a semiconductor process and a need for various thicknesses of a film. However, in an existing sulfonic ester, a residual not being dissolved in a developer may be generated on a bottom of a substrate when the thickness of the film is relatively great. When the sulfonic ester having an excellent affinity for the developer is used in order to remove the residual, large areas of the unexposed portion may be lost. Also, when the development speed is reduced in order to prevent a film loss occurring in the unexposed portion, greater exposure energy may be needed.

SUMMARY

An aspect of the present invention provides a photosensitive compound that may have an excellent sensitivity, and improve a residual film ratio.

Another aspect of the present invention provides a photosensitive composition including the photosensitive compound that may improve a perpendicularity of a pattern created after a semiconductor photolithography process.

Another aspect of the present invention also provides a method of manufacturing the photosensitive compound that may manufacture the photosensitive compound with a high efficiency.

According to an aspect of the present invention, there is provided a photosensitive compound composed of a naphthoquinonediazide sulfonic ester compound having at least one naphthoquinonediazide sulfoxy group, and having at least one carboxy group with 1 to 8 carbon atoms in one molecule or at least one alkoxy group with 1 to 8 carbon atoms in one molecule.

In this instance, the naphthoquinonediazide sulfonic ester compound may be represented by

[Chemical Formula 1]

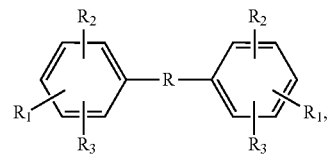

where $R_1$, $R_2$, and $R_3$ separately represent any one of a hydrogen atom, a halogen atom, an alkyl group with 1 to 8 carbon atoms, an ether group with 1 to 8 carbon atoms, an ester group with 1 to 8 carbon atoms, an alkoxy group with 1 to 8 carbon atoms, a carboxy group with 1 to 8 carbon atoms, a thioether group with 1 to 8 carbon atoms, and a naphthoquinonediazide sulfoxy group (-ODNQ), and R represents at least one compound group selected from a group represented by the following Chemical Formulas 1A to 1L,

 (1A)

 (1B)

 (1C)

 (1D)

 (1E)

 (1F)

 (1G)

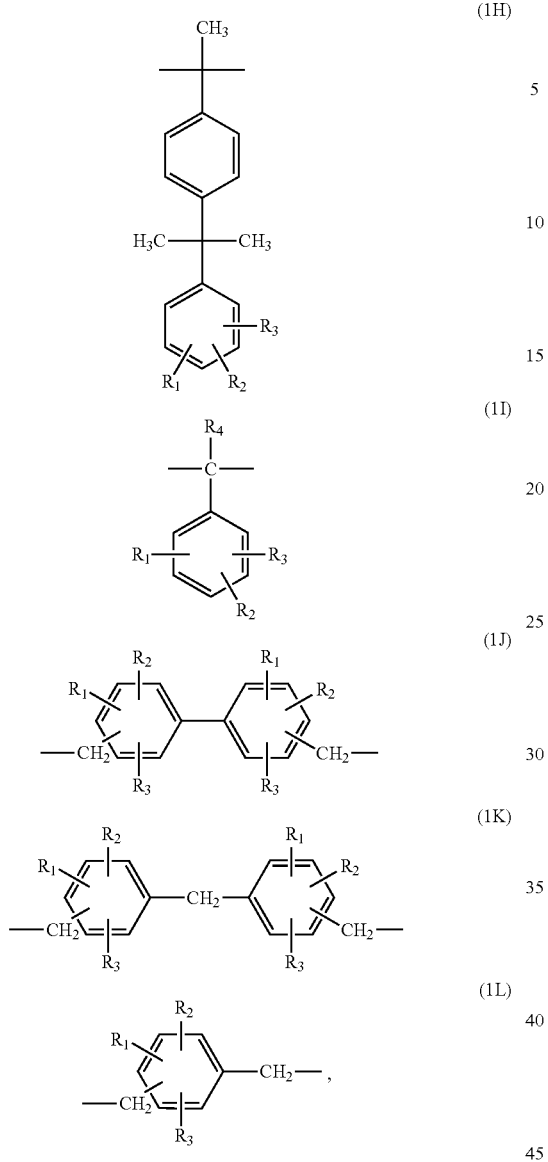

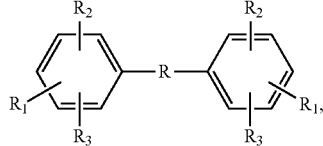

where R₁, R₂, and R₃ of 1H to 1L separately represent any one of the hydrogen atom, the halogen atom, the alkyl group with 1 to 8 carbon atoms, the ether group with 1 to 8 carbon atoms, the ester group with 1 to 8 carbon atoms, the alkoxy group with 1 to 8 carbon atoms, the carboxy group with 1 to 8 carbon atoms, the thioether group with 1 to 8 carbon atoms, and the naphthoquinonediazide sulfoxy group (-ODNQ), and R₄ of 1I represents a hydrogen atom or an alkyl group with 1 to 8 carbon atoms.

According to another aspect of the present invention, there is provided a photosensitive composition, including: at least one resin selected from a group consisting of a novolac derivative, a polyhydroxystyrene derivative, an acrylic acid-containing polyacrylate derivate, an (meth) acrylic acid derivative, a styrene derivate, a polyamide derivative, a polyimide derivate, and a poly vinyl pyrrolidone derivate; and a photosensitive compound represented by Chemical Formula 1 below. In this instance, about 1.0 mol to about 4.8 mol of a substituted portion substituted by a naphthoquinonediazide sulfoxy group (-ODNQ), and about 0.2 mol to about 4.0 mol of a substituent group substituted by either a carboxy group or an alkoxy group may be present with respect to 1 mol of the photosensitive compound existing within the whole composition. Also, the Chemical Formula 1 may be represented by where R₁, R₂, and R₃ separately represent any one of a hydrogen atom, a halogen atom, an alkyl group with 1 to 8 carbon atoms, an ether group with 1 to 8 carbon atoms, an ester group with 1 to 8 carbon atoms, an alkoxy group with 1 to 8 carbon atoms, a carboxy group with 1 to 8 carbon atoms, a thioether group with 1 to 8 carbon atoms, and a naphthoquinonediazide sulfoxy group (-ODNQ), and R represents at least one compound group selected from a group represented by the following Chemical Formulas 1A to 1L,

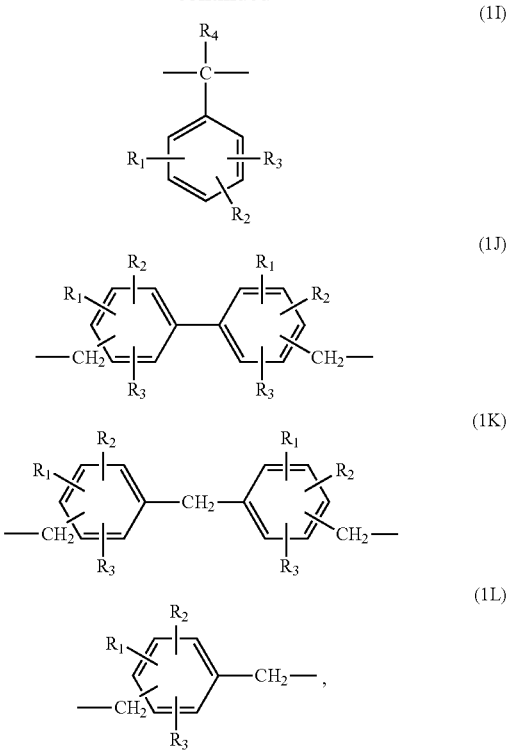

where $R_1$, $R_2$, and $R_3$ of 1H to 1L separately represent any one of the hydrogen atom, the halogen atom, the alkyl group with 1 to 8 carbon atoms, the ether group with 1 to 8 carbon atoms, the ester group with 1 to 8 carbon atoms, the alkoxy group with 1 to 8 carbon atoms, the carboxy group with 1 to 8 carbon atoms, the thioether group with 1 to 8 carbon atoms, and the naphthoquinonediazide sulfoxy group (-ODNQ), and $R_4$ of 1I represents a hydrogen atom or an alkyl group with 1 to 8 carbon atoms.

Also, the photosensitive compound may be contained in an amount of about 1 wt % to about 30 wt % with respect to the whole composition. Also, the composition may include a plurality of photosensitive compounds in which a substituted ratio by the naphthoquinonediazide sulfoxy group (-ODNQ) in a molecule and a substituted ratio by the carboxy group or the alkoxy group in a molecule are different from each other.

According to still another aspect of the present invention, there is provided a method of manufacturing a photosensitive compound, including: preparing a reactant by cooling a reactive solution including at least two phenol type hydroxyl group-containing compound and naphthoquinonediazide sulfonyl chloride (-DNQ-Cl) to about 10° C. or less, and adding, to the cooled reactive solution, any one of an alkyl anhydride, an aryl anhydride, and an alkoxy anhydride under a basic catalyst; and agitating the reactant at room temperature, and obtaining a precipitate generated by mixing the reactant and an excess amount of distilled water. In this instance, an amount of the naphthoquinonediazide sulfonyl chloride used may be adjusted so that naphthoquinonediazide sulfonyl chloride is partially substituted.

Also, the preparing of the reactant may include preparing a first reactant by cooling the reactive solution including the at least two phenol type hydroxyl group-containing compound and the naphthoquinonediazide sulfonyl chloride (-DNQ-Cl) to about 10° C. or less, and by reacting the at least two phenol type hydroxyl group-containing compound with the naphthoquinonediazide sulfonyl chloride (-DNQ-Cl) under a first basic catalyst; and preparing a second reactant by adding, to the prepared first reactant, any one of the alkyl anhydride, the aryl anhydride, and the alkoxy anhydride, and by reacting the generated first reactant with any one of the alkyl anhydride, the aryl anhydride, and the alkoxy anhydride at a temperature of about 10° C. or less and under a second basic catalyst.

Additional aspects, features, and/or advantages of the invention will be set forth in part in the description which follows and, in part, will be apparent from the description, or may be learned by practice of the invention.

EFFECT

According to exemplary embodiments, a photosensitive composition having a photosensitive compound may improve a solubility performance of an exposed portion while preventing a loss of an unexposed portion, thereby improving a pattern perpendicularity in a semiconductor photolithography process.

DETAILED DESCRIPTION

Hereinafter, a positive type photosensitive composition according to exemplary embodiments will be described in detail.

Naphthoquinonediazide sulfonic ester (hereinafter, referred to as DNQ-sulfonic ester) compound may be obtained by reacting at least two phenol type hydroxyl group-containing compound with naphthoquinonediazide sulfonyl chloride (-DNQ-Cl) under a basic catalyst, i.e,

[Chemical Equation 1]

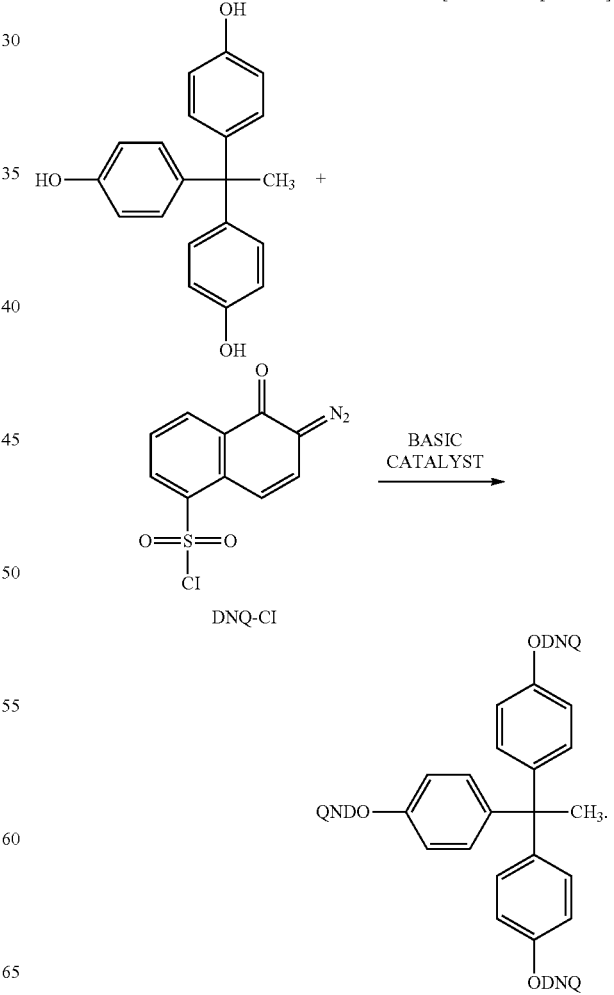

In Chemical Equation 1, when substituting a hydroxyl group with DNQ-C1 overall, a significantly excellent dissolution suppressing effect may be acquired. However, there may arise problems in that the DNQ-sulfonic ester compound is not easily dissolved in a resist solvent, and a residual is created on a bottom of a substrate after exposing and developing. In order to overcome these problems, a mixture of a trisubstituted compound, a disubstituted compound, and a monosubstituted compound may be used by utilizing about 2.5 mol of the DNQ-C1 instead of utilizing 3 mol of the DNQ-C1. As a substituted mole number of the DNQ-C1 is reduced, a solubility performance with respect to a solvent may be improved and the residual created on the substrate bottom may be reduced. In addition, exposure energy may be relatively reduced in comparison with that when the trisubstituted compound is solely used. When the substituted mole number of the DNQ-C1 is reduced, a residual film thickness after exposing and developing may be reduced. As the substituted mole number is reduced, the film thickness may be further reduced. Accordingly, an amount of substitution may be preferably about 2.5 mol to about 2.8 mol. Also, when a solvent well dissolving sulfonic ester is used, the amount of substitution may be about 2.8 mol or more, however, resulting in a residual created on the substrate bottom.

A photosensitive compound according to an exemplary embodiment may be the DNQ-sulfonic ester compound having at least one naphthoquinonediazide sulfoxy group (-ODNQ), and either at least one alkyl carbonyl group with 1 to 8 carbon atoms or at least one aryl carbonyl group, in one molecule.

More specifically, the DNQ-sulfonic ester compound may be represented by

[Chemical Formula 1]

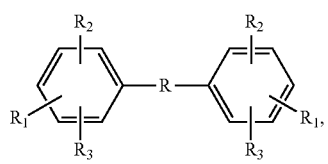

where $R_1$, $R_2$, and $R_3$ separately represent any one of a hydrogen atom, a halogen atom, an alkyl group with 1 to 8 carbon atoms, an ether group with 1 to 8 carbon atoms, an ester group with 1 to 8 carbon atoms, an alkoxy group with 1 to 8 carbon atoms, a carboxy group with 1 to 8 carbon atoms, a thioether group with 1 to 8 carbon atoms, and a naphthoquinonediazide sulfoxy group (-ODNQ), and R represents at least one compound group selected from a group represented by the following Chemical Formulas 1A to 1L,

 (1A)

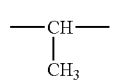 (1B)

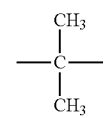 (1C)

-continued

 (1D)

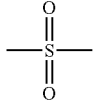 (1E)

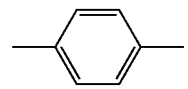 (1F)

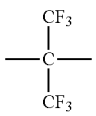 (1G)

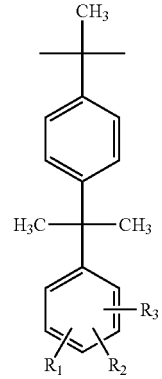 (1H)

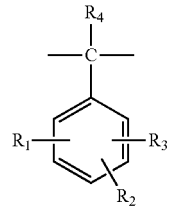 (1I)

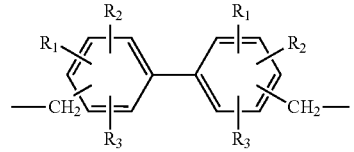 (1J)

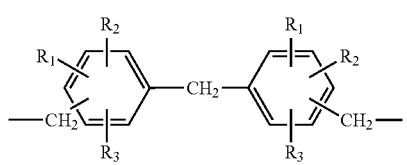 (1K)

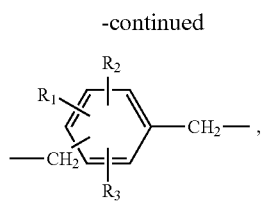

(1L)

where $R_1$, $R_2$, and $R_3$ of 1H to 1L separately represent any one of the hydrogen atom, the halogen atom, the alkyl group with 1 to 8 carbon atoms, the ether group with 1 to 8 carbon atoms, the ester group with 1 to 8 carbon atoms, the alkoxy group with 1 to 8 carbon atoms, the carboxy group with 1 to 8 carbon atoms, the thioether group with 1 to 8 carbon atoms, and the naphthoquinonediazide sulfoxy group (-ODNQ), and $R_4$ of 1I represents a hydrogen atom or an alkyl group with 1 to 8 carbon atoms.

The photosensitive compound may be generated by substituting a phenol type hydroxyl group with a DNQ group and with either a carboxy group or an alkoxy group in order to maximize the dissolution suppressing effect while minimizing the reduction in the thickness after developing. In general, the DNQ group may be transformed by incoming ultraviolet as in Chemical Equation 2 below to thereby improve a transmittance with respect to the ultraviolet, however, a residual may be created on the substrate due to a relatively lower transmittance in comparison with that when the DNQ group is less used.

[Chemical Equation 2]

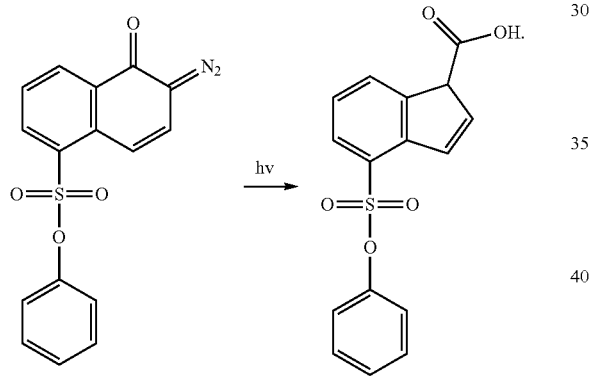

According to the present invention, since the dissolution suppressing effect is disadvantageously reduced when reducing an amount of substitution of DNQ in order to improve the transmittance, the remaining phenol type hydroxyl group may be substituted with the carboxy group or the alkoxy group for the purpose of overcoming the above disadvantage, which is represented by

[Chemical Equation 3]

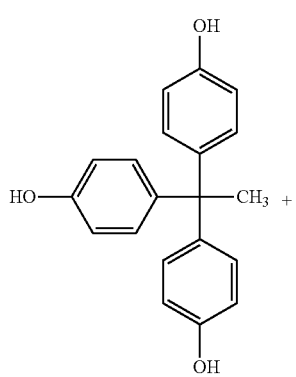

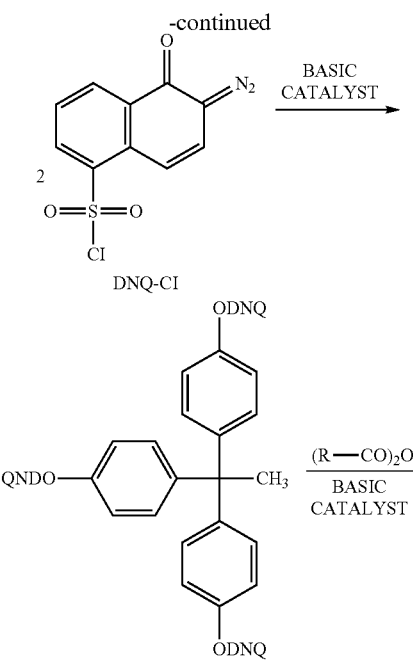

where R represents an aryl group with 1 to 8 carbon atoms or an alkyl group with 1 to 8 carbon atoms. In Chemical Equation 3, a reaction with respect to a compound having three hydroxyl groups is illustrated.

In Chemical Equation 3, an amount of the DNQ group and an amount of alkyl carbonyl group or aryl carbonyl group may be adjustable. However, when 1 mol or less of the DNQ group is substituted, and 2 mol or more of either the alkyl carbonyl group or the aryl carbonyl group is substituted, a dissolving speed with respect to a basic developer may be reduced, and thereby a lower portion of a film may be not developed in a case of the film having a great thickness. When 2.8 mol or more of the DNQ group is substituted, and 0.2 mol or less of either the alkyl carbonyl group or the aryl carbonyl group is substituted, a residual may be created on a substrate of the film after developing. An amount of substitution of the DNQ group may be most preferably about 1.0 mol to about 2.8 mol. The amount of the substation of the DNQ group may be appropriately adjusted based on a thickness of the film, an exposure energy, and the like.

A synthesis of the sulfonic ester may be performed in a similar manner as that when the DNQ group is introduced in the at least two phenol type hydroxyl group-containing compound. In some cases, a first reaction and a second reaction are separately performed, or simultaneously performed. A general reaction may be carried out by dissolving the at least two phenol type hydroxyl group-containing compound and the DNQ-C1 in a solvent to prepare a mixture, by cooling the prepared mixture down to about 10° C. or less, and by slowly dropping a basic catalyst. Next, after the dropping, the reaction may be further carried out by agitation at room temperature for a sufficient period of time, by dropping an alkyl anhydride or an aryl anhydride, and by slowly dropping the basic catalyst at about 10° C. Next, after the dropping, the reaction may be further carried out by agitation at room temperature for a sufficient period of time to obtain a reaction mixture, and by dropping the obtained reaction mixture on an excess amount of distilled water to obtain a final product as a precipitate. In this instance, the obtained final product may be vacuum-dried at a temperature of about 40° C. or less, and used in manufacturing the photosensitive composition.

A solvent used in the above described reaction may not be particularly limited, however, may be a solvent which does not participate in the reaction while is well dissolving a compound such as dioxane, tetrahydrofuran, dichloromethane, chloroform, and the like. A reaction time may slightly differ depending on a compound structure, however, the reaction may proceed by 90% or more for about 5 hours or more at room temperature. As the basic catalyst, a tertiary amine catalyst or a tertiary pyridine catalyst may be used. In this instance, a reaction speed of the tertiary amine catalyst may be slightly faster than that of the tertiary pyridine catalyst. Other basic catalysts may be used as long as the basic catalyst is not directly reacted with the DNQ-C1. However, as for a metal compound, a metal element may be required to be completely eliminated after the reaction. The obtained final product may be used in a mixture type having different amounts of substitution. A reaction degree can be seen using a high performance liquid chromatography (HPLC) or $^1$H-NMR. The photosensitive composition may be manufactured by dissolving, in a solvent, a resin being well dissolved in a basic developer, the DNQ-sulfonic ester compound, and some of additives. When the resin is rapidly dissolved in the basic developer, a used amount of the sulfonic ester may be increased, thereby reducing an amount of film loss of an unexposed portion after developing. However, when the used amount of the sulfuric ester compound is increased, a film transmittance may be reduced, and thereby a perpendicularity of a generated pattern may be reduced, or a residual may be created on the substrate. A speed in which the resin is dissolved in the basic developer may differ depending on applications of the photosensitive composition. The resin may not be particularly limited, however, as specific examples of the resin, there may be given resins that are dissolved in the basic developer such as novolac resin, polyhydroxystyrene, acrylic acid-containing polyacrylate, a copolymer with styrene, polyamide, polyimide, poly vinyl pyrrolidone, and the like. The solvent may not be particularly limited, however, as specific examples of the solvent, there may be given propylene glycol methyl ether acetate, gamma-butyrolactone, 2-heptanone, cyclohexanone, methoxy acetoxypropane, ethyl cellosolve acetate, butyl acetate, ethyl lactate, ethyl ethoxy propionate, methyl methoxy propionate, xylene, and the like. In this instance, when volatility of the solvent is too strong, coating flatness may be reduced, and when the volatility is too weak, a solvent residual on the film may increase. Depending on a thickness of the film and applications of the film, at least one solvent may be selected and used.

A total amount of solids used in the photosensitive composition may be relay on the film thickness. An amount of the sulfonic ester may be used by 5% to 50% based on the resin. The amount of the sulfonic ester used may differ depending on a dissolving speed of the resin with respect to the basic developer. When the dissolving speed of the resin with respect to the basic developer is superior, the amount of the sulfonic ester may be required to increase in order to prevent the film loss of the unexposed portion. As other elements used in the photosensitive composition, a ultraviolet sensitizer, a plasticizer with anti-crack properties, a surfactant for improving a flatness, some of additives for adjusting sensitivity, and the like may be given. As an additive for improving a developing speed, a carboxylic acid-containing pyridines or phenol type hydroxyl group-containing low molecular compound may be used.

Using the manufactured photosensitive composition, a film may be uniformly formed on the substrate by rotation coating, spray coating, slit coating, and the like regardless of the substrate. The formed film may be heated to about 60° C. to about 160° C. for 30 to 300 seconds to remove the residual solvent. The film from which the residual solvent is removed may be exposed to ultraviolet having passing through a mask to thereby obtain a desired pattern. The film exposed to the ultraviolet may be subjected to the above described heating process again for optimizing a pattern form, as necessary. The film may be developed using the basic developer, and washed using deionized water to thereby obtain a clean pattern. As the basic developer, a tetramethylammonium hydroxyl aqueous solution may be generally used, however, a sodium hydroxide aqueous solution, a potassium hydroxide aqueous solution, sodium carbonate, potassium carbonate, amines, pyridines, and the like may be selected and used depending on a size of the pattern and a work environment.

The photosensitive composition according to the present invention may minimize an amount of the energy for exposure, thereby reducing an exposure time, and minimizing the film loss of the unexposed portion.

Hereinafter, the present invention will be described in detail by examples. It is to be understood, however, that these examples are for illustrative purpose only, and are not construed to limit the scope of the present invention.

Synthesis Example 1

Novolac Resin Synthesis Example/Resin A m-cresol 70 g, p-cresol 60 g, and 2,5-xylenol 15 g were put in a round flask, and oxalic acid 5 g and hydrochloric acid solution (35%) 0.3 g both acting as a reaction catalyst were added in the flask to be agitated for 10 minutes at room temperature. Next, acetaldehyde 15 g and formalin aqueous solution (37%) 60 g were slowly dropped on the flask after the reactants were evenly mixed, and were agitated at about 90° C. for 8 hours. After a reaction partially proceeded, an internal temperature was raised to about 180° C. to remove water mixed in the reactant. When no more water was removed, the internal temperature was raised to about 195° C. to remove a non-reacted monomer. In this instance, a degree of vacuum was increased to the maximum to remove low molecules and the monomer included in a novolac resin to the maximum. The novolac resin of 130 g obtained through the above described process had a molecular weight in terms of polystyrene of 3,800, and had a degree of dispersion of 2.8.

Synthesis Example 2

Polyvinylpenol Derivative Synthesis/Resin B

Polyvinylpenol 50 g having a molecular weight of 8,000 and a degree of dispersion of 1.1 was dissolved in acetone 250 g in a round flask. Next, acetic anhydride 10 g was put in the flask, and triethylamine 12 g was slowly dropped at room temperature. Next, this solution was agitated at the same temperature for 5 hours, and an excess amount of deionized water including hydrochloric acid of 1% was slowly dropped to obtain a precipitate. Next, the obtained precipitate was vacuum-dried to obtain a resin 52 g in which a hydroxyl group of the polyvinylpenol was partially substituted with an acetic group. The obtained resin had a molecular weight in terms of polystyrene of 8,900, and had a degree of dispersion of 1.1.

Synthesis Example 3

Polyacrylate Synthesis/Resin C

In a round flask, styrene 5 g, 2-hydroxyethyl methacrylate 3 g, isobornyl methacrylate 10 g, and methacrylic acid 2 g were dissolved in iso-propanol 30 g, AIBN 3 g acting as a radical initiator was put in the flask, and an internal temperature of the flask was heated to about 80° C. Next, this solution was agitated at the same temperature for 5 hours, and was cooled down to the room temperature. Next, an excess amount of hexane was slowly dropped on the flask to obtain a white precipitate. Next, the obtained precipitate was filtered and vacuum-dried to synthesize a polyacrylate resin of 18 g having a molecular weight in terms of polystyrene of 16,000 and having a degree of dispersion of 2.2.

Synthesis Example 4

4,4'-oxybisbenzoic chloride Synthesis

In a flask of 0.5 L including an agitator and a thermometer mounted thereon, 4,4'-oxybisbenzoic acid 60 g (0.2324 mol) was added to N-methylpyrrolidone (NMP) 240 g, and these reactants were agitated and dissolved. Next, the flask was cooled down to 0° C., and thionyl chloride 110 g (0.9246 mol) was dropped on the flask to be reacted for one hour to thereby obtain a 4,4'-oxybisbenzoic chloride solution.

Synthesis Example 5

Polyamide Synthesis/Resin D

NMP 400 g was put in a flask of including an agitator and a thermometer mounted thereon, 2,2-bis(3-amino-4-hydroxyphenyl) hexafluoropropane 85 g (0.2321 mol) was added to the flask, and these reactants were agitated to be dissolved. Next, pyridine 39 g (0.4930 mol) was added to the flask, 5-norbonen-2,3-dicarboxylic acid anhydride 8 g (0.0487 mol) and the 4,4'-oxybisbenzoic chloride solution were slowly dropped on the flask, and were agitated at room temperature for one hour. Next, a solution obtained through the above described process was added in water of 3 L to obtain a precipitate. Next, the precipitate was filtered, washed, and vacuum-dried to obtain polyamide 110 g. In this instance, the obtained polyamide had an average molecular weight in terms of polystyrene of 18,500, and had a degree of dispersion of 1.9.

Synthesis Example 6 dimethyl-3,3',4,4'-diphenyl ether-tetracarboxylate dichloride Synthesis

Dimethyl-3,3',4,4'-diphenyl ether-tetracarboxylic acid anhydride 60 g (0.1934 mol), methyl alcohol 12.5 g (0.3901 mol), triethylamine 2 g (0.0198 mol), and NMP 120 g were added in a flask of including an agitator and a thermometer mounted thereon, and were agitated and reacted at room temperature for 4 hours to obtain a di-n-methyl-3,3',4,4'-diphenyl ether-tetracarboxylate solution. Next, the flask was cooled down to about 0° C., thionyl chloride 70 g (0.5884 mol) was dropped on the flask to be reacted for two hours to thereby obtain a dimethyl-3,3',4,4'-diphenyl ether-tetracarboxylate dichloride solution.

Synthesis Example 7

NMP 260 g was put in a flask of including an agitator and a thermometer mounted thereon, 2,2-bis(3-amino-4-hydroxyphenyl) hexafluoropropane 65 g (0.1775 mol) was added to the flask, and these reactants were agitated to be dissolved. Next, pyridine 35 g (0.4425 mol) was added to the flask, and the dimethyl-3,3',4,4'-diphenyl ether-tetracarboxylate dichloride solution was slowly dropped on the flask for 30 minutes, and these reactants were agitated for one hour at room temperature. Three liters of water was added to a solution obtained through the above described process to obtain a precipitate. Next, the obtained precipitate was filtered, washed, and vacuum-dried to obtain polyamidate 128 g. In this instance, the polyamidate had an average molecular weight in terms of polystyrene of 19,200, and had a degree of dispersion of 1.7.

Comparative Synthesis Example 1

Sulfonic Ester Synthesis/PAC A

In a round flask, tris (4-hydroxypenyl)ethane 50 g and 1,2-naphthoquinonediazide-5-sulfonic chloride 132 g were dissolved in dioxane 900 g, and was cooled using ice water. Next, triethylamine 48 g was slowly dropped on this solution at the same temperature, and the solution was agitated for 8 hours at room temperature. Next, the agitated solution was dropped on an excess amount of deionized water to obtain a precipitate. Next, the obtained precipitate was filtered, washed, and vacuum-dried at about 40° C. for 48 hours to thereby obtain sulfonic ester 118 g.

Comparative Synthesis Example 2

Sulfonic Ester Synthesis/PAC B

In a round flask, tris (4-hydroxypenyl)ethane 50 and 1,2-naphthoquinonediazide-5-sulfonic chloride 109 g were dissolved in dioxane 800 g, and was cooled using ice water. Next, triethylamine 46 g was slowly dropped on this solution at the same temperature, and the solution was agitated for 8 hours at room temperature. Next, the agitated solution was dropped on an excess amount of deionized water to obtain a precipitate. Next, the obtained precipitate was filtered, washed, and vacuum-dried at about 40° C. for 48 hours to thereby obtain sulfonic ester 110 g.

Synthesis Example 8

Sulfonic Ester Synthesis/PAC C

In a round flask, tris (4-hydroxypenyl)ethane 50 g, 1,2-naphthoquinonediazide-5-sulfonic chloride 87 g, and acetic anhydride 17 g were dissolved in dioxane 800 g, and was cooled using ice water. Next, triethylamine 59 g was slowly dropped on this solution at the same temperature, and the solution was agitated for 8 hours at room temperature. Next, the agitated solution was dropped on an excess amount of deionized water to obtain a precipitate. Next, the obtained precipitate was filtered, washed, and vacuum-dried at about 40° C. for 48 hours to thereby obtain sulfonic ester 95 g.

Synthesis Example 9

Sulfonic Ester Synthesis/PAC D

In a round flask, tris (4-hydroxypenyl)ethane 50 g, 1,2-naphthoquinonediazide-5-sulfonic chloride 65 g, and acetic anhydride 25 g were dissolved in dioxane 800 g, and was cooled using ice water. Next, triethylamine 59 g was slowly dropped on this solution at the same temperature, and the solution was agitated for 8 hours at room temperature. Next, the agitated solution was dropped on an excess amount of deionized water to obtain a precipitate. Next, the obtained precipitate was filtered, washed, and vacuum-dried at about 40° C. for 48 hours to thereby obtain sulfonic ester 88 g.

Synthesis Example 10

Sulfonic Ester Synthesis/PAC E

In the comparative synthesis example 1, sulfonic ester 91 g was obtained using 1,2-naphthoquinonediazide-4-sulfonic chloride 87 g instead of using the 1,2-naphthoquinonediazide-5-sulfonic chloride 87 g.

Synthesis Example 11

Sulfonic Ester Synthesis/PAC F

In the synthesis example 9, sulfonic ester 86 g was obtained using 1,2-naphthoquinonediazide-4-sulfonic chloride 65 g instead of using the 1,2-naphthoquinonediazide-5-sulfonic chloride 65 g.

Synthesis Example 11

Sulfonic Ester Synthesis/PAC G

In the synthesis example 9, sulfonic ester 90 g was obtained using butyric anhydride 38 g instead of using the acetic anhydride 25 g.

Synthesis Examples 13 to 16

Using chemical formulas below of ballast, PAC H (synthesis example 13), PAC I (synthesis example 14), PAC J (synthesis example 15), and PAC K (synthesis example 16) were obtained in the same equivalence ratio and synthesis method as those in the synthesis example 9.

[Chemical formulas 2A to 2D]

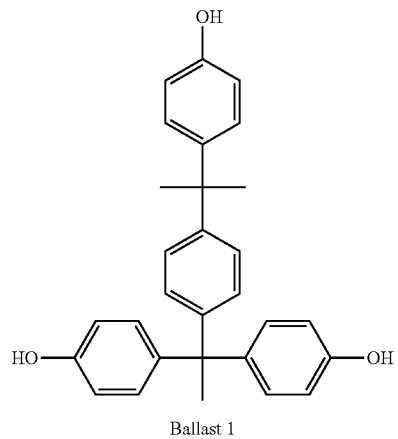

Ballast 1

(2A)

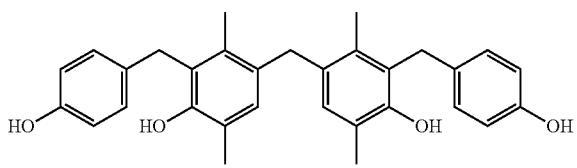

Ballast 2

(2B)

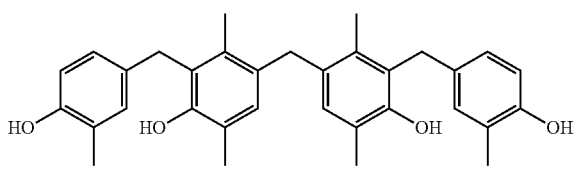

Ballast 3

(2C)

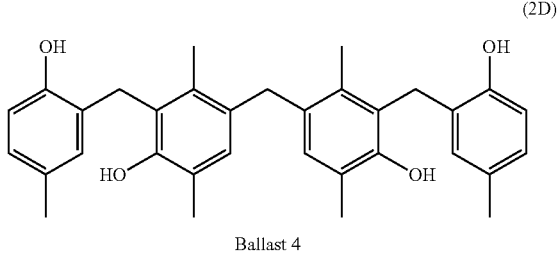

Ballast 4

(2D)

The PAC H was a compound synthesized in the ballast 1, the PAC I was a compound synthesized in the ballast 2, the PAC J was a compound synthesized in the ballast 3, and the PAC K was a compound synthesized in the ballast 4.

Examples 1 to 13 and Comparative Examples 1 and 2

With respect to alkali-soluble resin 100 g, a sulfonic ester compound 25 g and a fluorinated surfactant 300 ppm for improving film uniformity were dissolved in a solvent 230 g, and this solution was filtered using a filter having a pore size of 0.5 μm to obtain a photoresist composition. In table below, composition ratios of compositions and results of examples could be seen. The compositions were heated to about 120° C. for 120 seconds, and dried to obtain a thickness of 7 μm after rotation-coating the compositions. These compositions were exposed using an i-line stepper, and developed using tetramethylammonium hydroxide of 2.38 wt % to obtain a pattern. A residual film ratio may be a value obtained by dividing a thickness of an unexposed portion after the developing by a thickness obtained by heating and drying the composition after the rotation coating.

TABLE

| | Composition | | | Residual film ratio (%) | Sensitivity (mJ/cm$^2$) | Resolution (μm) | Pattern perpendicularity |
|---|---|---|---|---|---|---|---|
| | Resin | Sulfonic ester | Solvent | | | | |
| Example 1 | A | PAC D | PGMEA | 89 | 250 | 2 | medium |
| Example 2 | B | PAC D | PGMEA | 90 | 270 | 1 | good |
| Example 3 | C | PAC D | PGMEA | 85 | 220 | 1 | medium |
| Example 4 | D | PAC D | GBL | 90 | 280 | 2 | good |
| Example 5 | E | PAC D | GBL | 90 | 300 | 2 | good |
| Comparative example 1 | D | PAC A | GBL | 90 | 520 | 3 | bad |
| Comparative example 2 | D | PAC B | GBL | 80 | 400 | 2 | bad |
| Example 6 | D | PAC C | GBL | 91 | 300 | 2 | good |
| Example 7 | D | PAC E | GBL | 88 | 270 | 2 | good |
| Example 8 | D | PAC F | GBL | 88 | 250 | 2 | good |
| Example 9 | D | PAC G | GBL | 95 | 330 | 2 | good |
| Example 10 | D | PAC H | GBL | 91 | 300 | 2 | good |
| Example 11 | D | PAC I | GBL | 90 | 260 | 2 | good |
| Example 12 | D | PAC J | GBL | 90 | 270 | 2 | good |
| Example 13 | D | PAC K | GBL | 90 | 270 | 2 | good |

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. A photosensitive compound composed of a naphthoquinonediazide sulfonic ester compound having at least one naphthoquinonediazide sulfoxy group, and having either at least one carboxy group with 1 to 8 carbon atoms or at least one alkoxy group with 1 to 8 carbon atoms, in one molecule, wherein the naphthoquinonediazide sulfonic ester compound is represented by

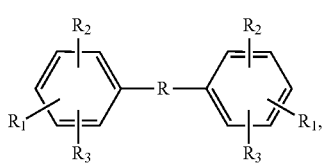

[Chemical Formula 1]

where $R_1$, $R_2$ and $R_3$ separately represent any one of a hydrogen atom, a halogen atom, an alkyl group with 1 to 8 carbon atoms, an ether group with 1 to 8 carbon atoms, an ester group with 1 to 8 carbon atoms, an alkoxy group with 1 to 8 carbon atoms, a carboxy group with 1 to 8 carbon atoms, a thioether group with 1 to 8 carbon atoms, and a naphthoquinonediazide sulfoxy group (-ODNQ), and R comprises $$-\underset{\underset{CH_3}{|}}{CH}-$$

2. A photosensitive composition, comprising:
at least one resin selected from a group consisting of a novolac derivative, a polyhydroxystyrene derivative, an acrylic acid-containing polyacrylate derivate, an (meth) acrylic acid derivative, a styrene derivate, a polyamide derivative, a polyimide derivate, and a poly vinyl pyrolidone derivate; and
a photosensitive compound represented by Chemical Formula 1, wherein
about 1.0 mol to about 4.8 mol of a substituted portion substituted by a naphthoquinonediazide sulfoxy group (-ODNQ), and about 0.2 mol to about 4.0 mol of a substituent group substituted by either a carboxy group or an alkoxy group are present with respect to 1 mol of the photosensitive compound existing within the whole composition, the Chemical Formula 1 being represented by

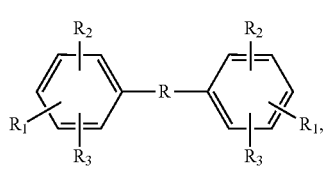

[Chemical Formula 1]

where $R_1$, $R_2$, and $R_3$ separately represent any one of a hydrogen atom, a halogen atom, an alkyl group with 1 to 8 carbon atoms, an ether group with 1 to 8 carbon atoms, an ester group with 1 to 8 carbon atoms, an alkoxy group with 1 to 8 carbon atoms, a carboxy group with 1 to 8 carbon atoms, a thioether group with 1 to 8 carbon atoms, and a naphthoquinonediazide sulfoxy group (-ODNQ), and R comprises

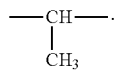

3. The photosensitive composition of claim 2, wherein the photosensitive compound is contained in an amount of about 1 wt % to about 30 wt % with respect to the whole composition.

4. The photosensitive composition of claim 2, wherein the composition includes a plurality of photosensitive compounds in which a substituted ratio by the naphthoquinonediazide sulfoxy group (-ODNQ) in a molecule and a substituted ratio by the carboxy group or the alkoxy group in a molecule are different from each other.

* * * * *